US 8,730,313 B2

(12) United States Patent
Numata

(10) Patent No.: US 8,730,313 B2
(45) Date of Patent: May 20, 2014

(54) ENDOSCOPE APPARATUS AND METHOD

(75) Inventor: Kenji Numata, Tokyo (JP)

(73) Assignee: Olympus Corporation, Tokyo (JP)

(*) Notice: Subject to any disclaimer, the term of this patent is extended or adjusted under 35 U.S.C. 154(b) by 485 days.

(21) Appl. No.: 12/689,504

(22) Filed: Jan. 19, 2010

(65) Prior Publication Data

US 2010/0182413 A1    Jul. 22, 2010

(30) Foreign Application Priority Data

Jan. 21, 2009    (JP) ................ P2009-011150

(51) Int. Cl.
A62B 1/04    (2006.01)

(52) U.S. Cl.
USPC .............. 348/65; 348/61; 348/74; 348/72

(58) Field of Classification Search
None
See application file for complete search history.

(56) References Cited

U.S. PATENT DOCUMENTS

| 5,377,253 | A | 12/1994 | Ifuku |
| 6,063,023 | A | 5/2000 | Sakiyama et al. |
| 7,048,685 | B2 * | 5/2006 | Sakiyama ............... 600/175 |
| 7,130,618 | B2 | 10/2006 | Yokoyama |
| 2008/0304724 | A1 * | 12/2008 | Eino ....................... 382/128 |
| 2009/0158315 | A1 * | 6/2009 | Bendall et al. ............ 725/32 |

FOREIGN PATENT DOCUMENTS

| JP | 63-201618 A | 8/1988 |
| JP | 02-244021 A | 9/1990 |
| JP | 05-329142 A | 12/1993 |
| JP | 10-248806 A | 9/1998 |
| JP | 2001-151775 A | 6/2001 |
| JP | 2003-070719 A | 3/2003 |
| JP | 2003-075136 A | 3/2003 |
| JP | 2003-230117 A | 8/2003 |
| JP | 2004-049638 A | 2/2004 |
| JP | 2004-313291 A | 11/2004 |
| JP | 2005-044004 A | 2/2005 |
| JP | 2006-061469 A | 3/2006 |
| JP | 2006-247371 A | 9/2006 |
| JP | 2006-334247 A | 12/2006 |
| JP | 2007-114456 A | 5/2007 |
| JP | 2007-171941 A | 7/2007 |

OTHER PUBLICATIONS

Japanese Office Action dated Apr. 9, 2013 (and English translation thereof) in counterpart Japanese Application No. 2009-011150.

* cited by examiner

Primary Examiner — Mehrdad Dastouri
Assistant Examiner — James Anderson, II
(74) Attorney, Agent, or Firm — Holtz, Holtz, Goodman & Chick, PC

(57) ABSTRACT

An endoscope apparatus includes: a reading unit which reads video data and control data from a recording medium, the recording medium containing the video data including a plurality of image data and the control data used to control a measurement operation; a measuring unit which performs the measurement operation on the basis of the image data of the video data read by the reading unit; and a control unit which controls the measuring unit on the basis of the control data read by the reading unit.

13 Claims, 7 Drawing Sheets

ENDOSCOPE APPARATUS AND METHOD

BACKGROUND OF THE INVENTION

1. Field of the Invention

The present invention relates to an endoscope apparatus and a method that processes a video signal obtained by imaging a subject.

Priority is claimed on Japanese Patent Application No. 2009-011150, filed Jan. 21, 2009, the content of which is incorporated herein by reference.

2. Description of the Related Art

An endoscope apparatus has been used in the industrial field. The endoscope apparatus includes a thin and long insertion portion of an endoscope. A user inserts the insertion portion into an internal space of an object to be inspected such as a jet engine or a pipe in a factory, and performs an observation of corrosion or damage of a region of the object to be inspected and various treatments thereon.

Generally, the endoscope apparatus includes an endoscope and an apparatus body to which the endoscope is connected. An imaging unit including an imaging device such as an imaging lens or a CCD is disposed in a distal end of the endoscope. The endoscope includes a thin and long insertion portion provided with an illumination unit having an LED or the like to illuminate the internal space of the object from the distal end of the endoscope. In addition, the apparatus body includes various units. In detail, the apparatus body includes electric parts, such as a driving unit for driving the imaging unit and an image processing unit for processing the image signal output from the imaging unit, and a power supply for the illumination of the light.

Japanese Unexamined Patent Application, First Publication No. S63-201618 discloses a three-dimensional measurement by using the endoscope. In detail, in a site of observation, when an endoscope image required for measurement is displayed, the endoscope image is frozen (paused), and measurement is performed by using the frozen endoscope image. Alternatively, the endoscope image required for measurement is recorded as a still image, and measurement is performed by using the still image.

SUMMARY OF THE INVENTION

An endoscope apparatus according to an aspect of the present invention includes a reading unit which reads video data and control data from a recording medium, the recording medium containing the video data including a plurality of image data and the control data used to control a measurement operation; a measuring unit which performs the measurement operation on the basis of the image data of the video data read by the reading unit; and a control unit which controls the measuring unit on the basis of the control data read by the reading unit.

DETAILED DESCRIPTION OF THE INVENTION

Figure 1:
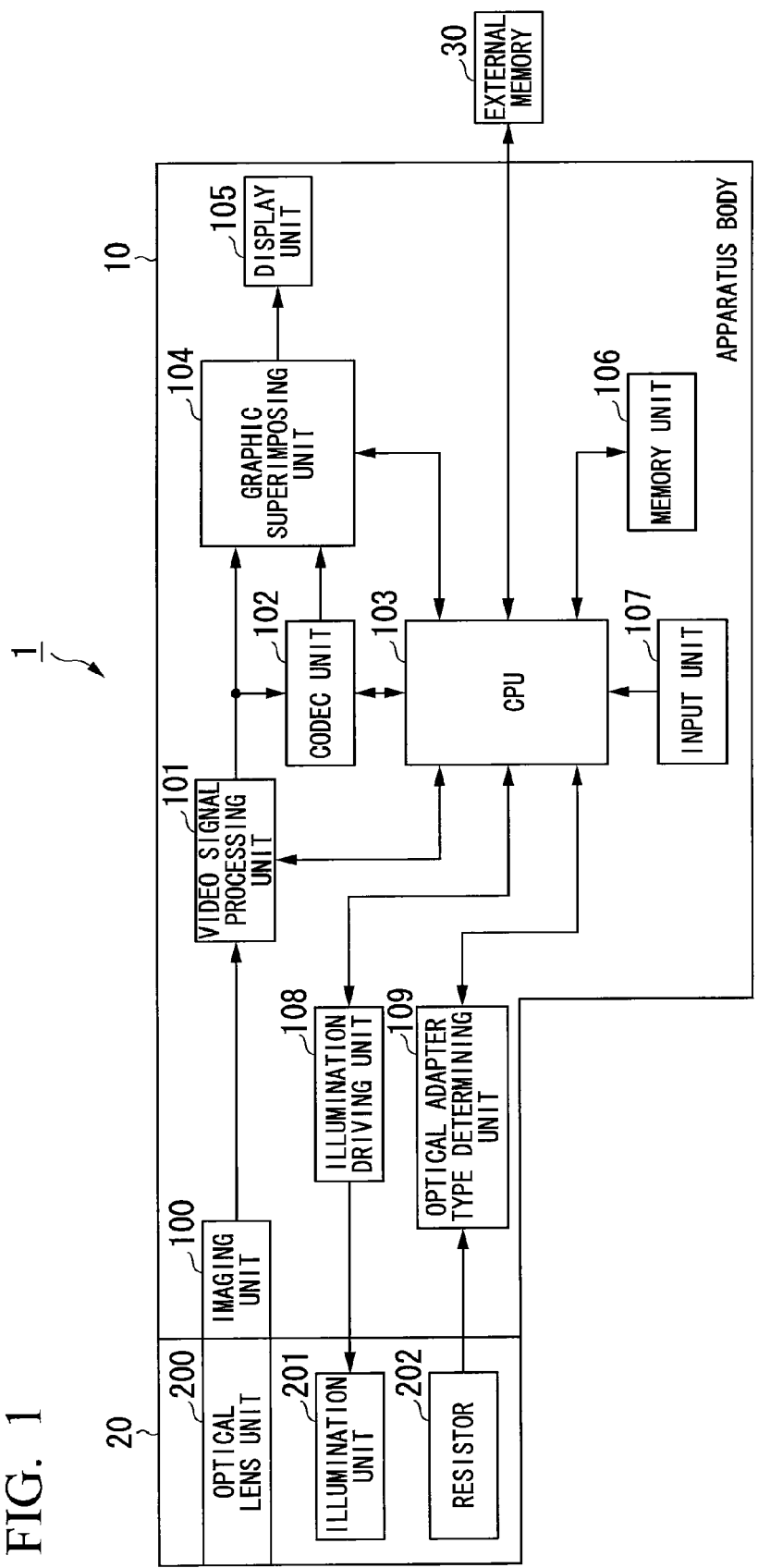
FIG. 1 is a block diagram showing a configuration of an endoscope apparatus according to an embodiment of the present invention.

Hereinafter, an embodiment of the present invention will be described with reference to the accompanying drawings. FIG. 1 is a block diagram showing a configuration of an endoscope apparatus according to the embodiment of the present invention. An endoscope apparatus 1 includes an apparatus body 10 having an insertion portion, and an optical adapter 20. The optical adapter 20 is detachably attached to a distal end of the insertion portion.

The apparatus body 10 includes an imaging unit 100, a video signal processing unit 101, a codec unit 102, a CPU 103, a graphic superimposing unit 104, a display unit 105, a memory unit 106, an input unit 107, an illumination driving unit 108, and an optical adapter type determining unit 109. The optical adapter 20 includes an optical lens unit 200, an illumination unit 201, and a resistor 202.

Light from a subject (an object to be measured) enters the optical lens unit 200, and forms a subject image by the optical lens unit 200. The subject image enters the imaging unit 100. The imaging unit 100 includes an imaging device such as a CCD, and captures the subject image to create a video signal. The video signal processing unit 101 performs a signal process such as a gain adjustment or a white balance on the video signal output from the imaging unit 100.

The video signal processed by the video signal processing unit 101 is output as video data to the graphic superimposing unit 104 and the codec unit 102. The video data includes a plurality of frames or fields of image data. The codec unit 102 performs a codec process (compression/decompression) such as a motion JPEG or MPEG on the video data, and performs a codec process such as JPEG on still image data which is image data corresponding to one frame or field of the video data.

The video data and the still image data created by the endoscope apparatus 1 may be recorded in an external memory 30 connected to the endoscope apparatus 1. In addition, the video data and the still image data recorded in the external memory 30 may be played on the endoscope apparatus 1. The codec unit 102 can compress the video data or the still image data in the case where the video data or the still image data is recorded in the external memory 30. The compressed video data or the still image data is recorded in the external memory 30 by the CPU 103. In the case of playing the video data or the still image data recorded in the external memory 30, the codec unit 102 decompresses the video data or the still image data read from the external memory 30 by the CPU 103, and plays the decompressed video data or the decompressed still image data.

The CPU 103 performs various processes for controlling the respective units of the apparatus body 10 by executing a program stored in the memory unit 106. The CPU 103 also performs measurement of geometric characteristics of the subject. In the case where the CPU 103 performs the measurement, the still image data input to the codec unit 102 is directly output to the CPU 103 without compression. The CPU 103 performs the measurement by using this still image data. In addition, the measurement may be performed by using the video data recorded in the external memory 30. In this case, the CPU 103 performs the measurement by using image data of any one frame or field which constitutes the video data recorded in the external memory 30.

The graphic superimposing unit 104 creates a display signal for displaying an image by superimposing graphic data created by the CPU 103 on the image data or the still image data, which constitutes the video data based on the video signal processed by the video signal processing unit 101, or on the image data or the still image data, which constitutes the video data played by the codec unit 102. By superimposing the graphic data on the image data of the endoscope image, it is possible to display a menu, a cursor, a measurement result, and the like together with the endoscope image. The display unit 105 displays a video or a still image on the basis of the display signal processed by the graphic superimposing unit 104.

The memory unit 106 includes a ROM which stores a program for controlling an operation of the CPU 103, and a RAM which temporarily stores data or the like used for various processes by the CPU 103. The input unit 107 includes an operation portion operated by a user, and outputs a signal based on the operation result of the operation portion to the CPU 103. The CPU 103 identifies a user's instruction on the basis of the signal output from the input unit 107, and performs various processes in accordance with the instruction.

The illumination driving unit 108 drives the illumination unit 201 in accordance with the instruction from the CPU 103. The illumination unit 201 illuminates the subject. The optical adapter type determining unit 109 detects a resistance value of the resistor 202 provided in the optical adapter 20, determines the type of optical adapter 20 corresponding to the resistance value, and then outputs to the CPU 103 optical adapter type data (optical system type data) showing the type of optical adapter.

Figure 2A:
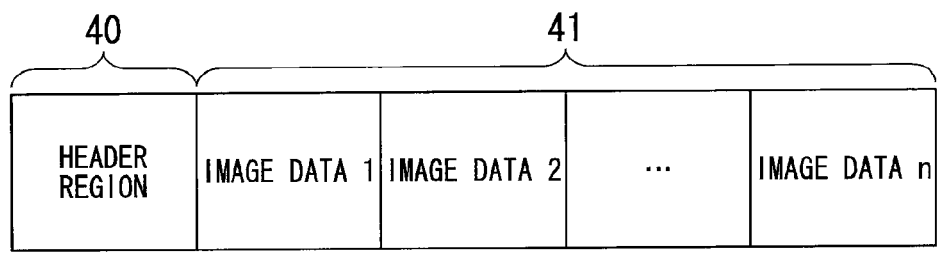
FIGS. 2A and 2B are reference diagrams showing a data format of video data according to the embodiment of the present invention.
Figure 2B:
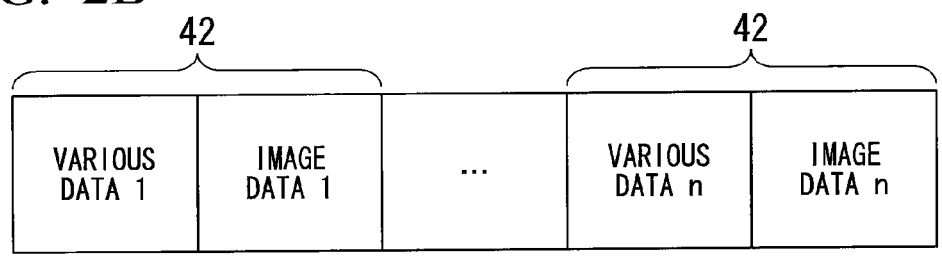

Next, a data format of the video data and the still image data according to this embodiment will be described. FIGS. 2A and 2B show the data format of the video data. In FIG. 2A, the video data includes a header region 40 and a data region 41. The data region 41 includes image data composed of a frame or field unit. In FIG. 2A, n frames or n fields of the image data constitute the data region 41. The header region 40 includes control data which has data corresponding to every frame or field of the image data constituting the data region 41. The control data will be described later in detail. In addition, in the case where measurement result data showing a measurement result is added to the video data, the header region 40 also includes the measurement result data. The measurement result data can include data of a measurement type, coordinates of a measurement point, and a measurement result.

In FIG. 2B, the video data includes unit data 42 composed of a frame or field unit. The unit data 42 includes image data and various data of a frame or field unit. The various data includes the control data, the measurement result data, and the like.

Figure 3:
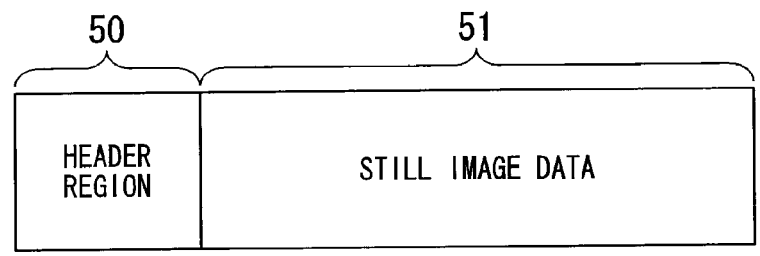
FIG. 3 is a reference diagram showing a data format of still image data according to the embodiment of the present invention.

FIG. 3 shows a data format of the still image data. The still image data includes a header region 50 and a still image data region 51. The header region 50 includes control data corresponding to the still image data portion 51. In addition, in the case where the measurement result is added to the still image data, the header region 50 also includes the measurement result data.

Next, the control data according to this embodiment will be described. The control data is data used for the control of the measurement operation. The control data can include a measurement-possible flag for showing whether or not the measurement is possible for every frame or field. The measurement-possible flag is used to determine whether or not the measurement is possible in the case where the video data recorded in the external memory 30 is played and the measurement is performed by using the video data.

The CPU 103 creates the measurement-possible flag on the basis of various states (for example, the type of optical adapter 20, the presence of image process which influences measurement accuracy, the format (frame/field) of the image data) of the endoscope apparatus. The type of optical adapter 20 is shown by the optical adapter type data created by the optical adapter type determining unit 109. In the case where the type of optical adapter 20 is applicable to the measurement (for example, the type of optical adapter 20 is a stereo measurement adapter capable of performing a three-dimensional measurement), the measurement is possible.

Examples of the image process which influences the measurement accuracy can include an electronic zoom, a noise reduction, an edge enhancement, and an interpolation. Currently, image data on which the above image processes are performed is not suitable for measurement. However, in the future, if the image processes are improved and the measurement accuracy is not degraded (or the measurement accuracy is improved) even when the image data subjected to the image processes is used, the image data subjected to the image processes may be used for measurement.

Regarding the format of the image data, the image data is suitable for measurement in the case where the obtained image data is composed of a frame unit, but the image data is not suitable for measurement in the case where the obtained image data is composed of a field unit. However, in the future, if the number of pixels increases and the measurement accuracy is not degraded even when image data composed of a field unit is used, the image data composed of a field unit may be used for measurement.

The CPU 103 creates the measurement-possible flag on the basis of the above-described contents. The standard for determining the measurement-possible state can be appropriately changed in accordance with the required measurement accuracy, for example, as below. In the case where the type of optical adapter 20 is not applicable to the measurement, the measurement-possible flag is set to a measurement impossible state regardless of the contents of other items (i.e., the presence of the image process and the format of the image data in this embodiment). In the case where the type of optical adapter 20 is applicable to the measurement, the measurement-possible flag is created in accordance with the contents of other items. Regarding the other items, the measurement-possible flag may be created on the basis of the contents of any one of the items, or the measurement-possible flag may be created on the basis of the contents obtained by combining plural items.

In addition, the control data can include the optical adapter type data together with the measurement-possible flag. In the measurement, correction data is used to correct optical distortion occurred in the image data. The optical distortion varies with the type of optical adapter 20. The correction data is prepared for each type of optical adapter 20, and is stored in the memory unit 106. At the time of measurement, on the basis of the optical adapter type data, the correction data corresponding to the type of optical adapter 20 is used. If using the correction data which does not correspond to the type of optical adapter 20, the measurement accuracy is degraded. In addition to the optical adapter type data, data showing the presence of the above-described image process or the format of the image data may be included as the control data.

Figure 4:
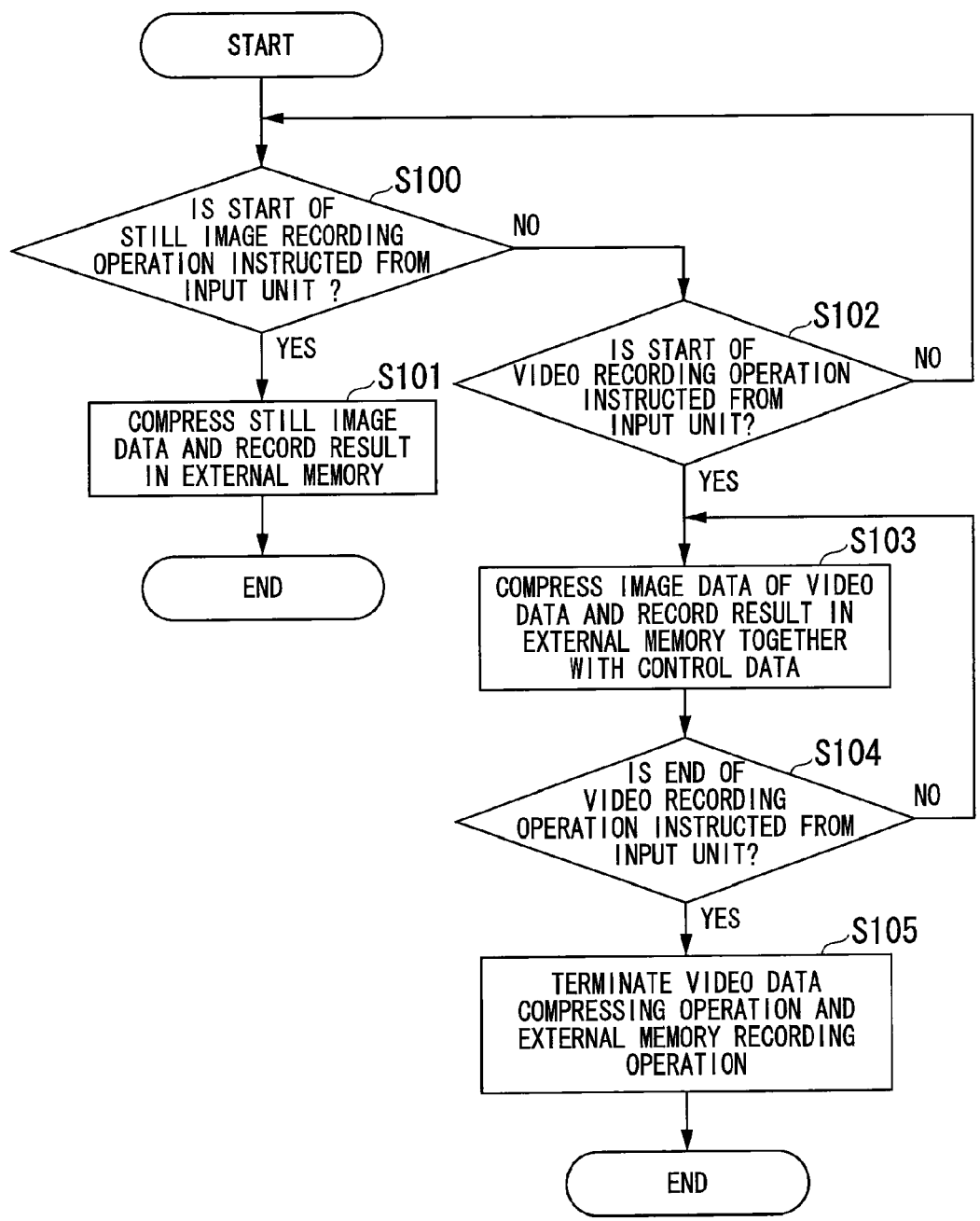
FIG. 4 is a flowchart showing a sequence of an operation (recording) of the endoscope apparatus according to the embodiment of the present invention.

Next, an operation of the endoscope apparatus 1 will be described. Since an operation of performing measurement while imaging a subject on site is the same as that of the related art, the description thereof will be omitted. FIG. 4 shows a sequence of an operation of recording video data and still image data. At the start time of the operation shown in FIG. 4, a video of the subject is captured and displayed on the display unit 105.

First, the CPU 103 determines whether or not the start of the still image recording operation is instructed by the user, on the basis of the signal output from the input unit 107 (Step S100). In the case where the start of the still image recording operation is instructed by the user, the CPU 103 compresses the still image data, which is image data of one frame or field of the video data, by using the codec unit 102, and records the compressed still image data in the external memory 30 (Step S101). With this process, the still image data recording operation completes.

In the case where the start of the still image recording operation is not instructed by the user, the CPU 103 determines whether or not the start of the video recording operation is instructed by the user, on the basis of the signal output from the input unit 107 (Step S102). In the case where the start of the video recording operation is not instructed by the user, the process returns to Step S100.

Further, in the case where the start of the video recording operation is instructed by the user, the CPU 103 compresses image data of one frame or field of the video data by using the codec unit 102, adds the control data corresponding to the frame or field to the compressed image data, and then records the result as a part of the video data in the external memory 30 (Step S103).

Subsequently, the CPU 103 determines whether or not the end of the video recording operation is instructed by the user, on the basis of the signal output from the input unit 107 (Step S104). In the case where the end of the video recording operation is not instructed by the user, the process returns to Step S103, and the video recording operation is continued. In the case where the end of the video recording operation is instructed by the user, the CPU 103 terminates the compression of the video data by the codec unit 102, and terminates the operation of recording the video data in the external memory 30 (Step S104). Thus, the video recording operation ends.

Figure 5:
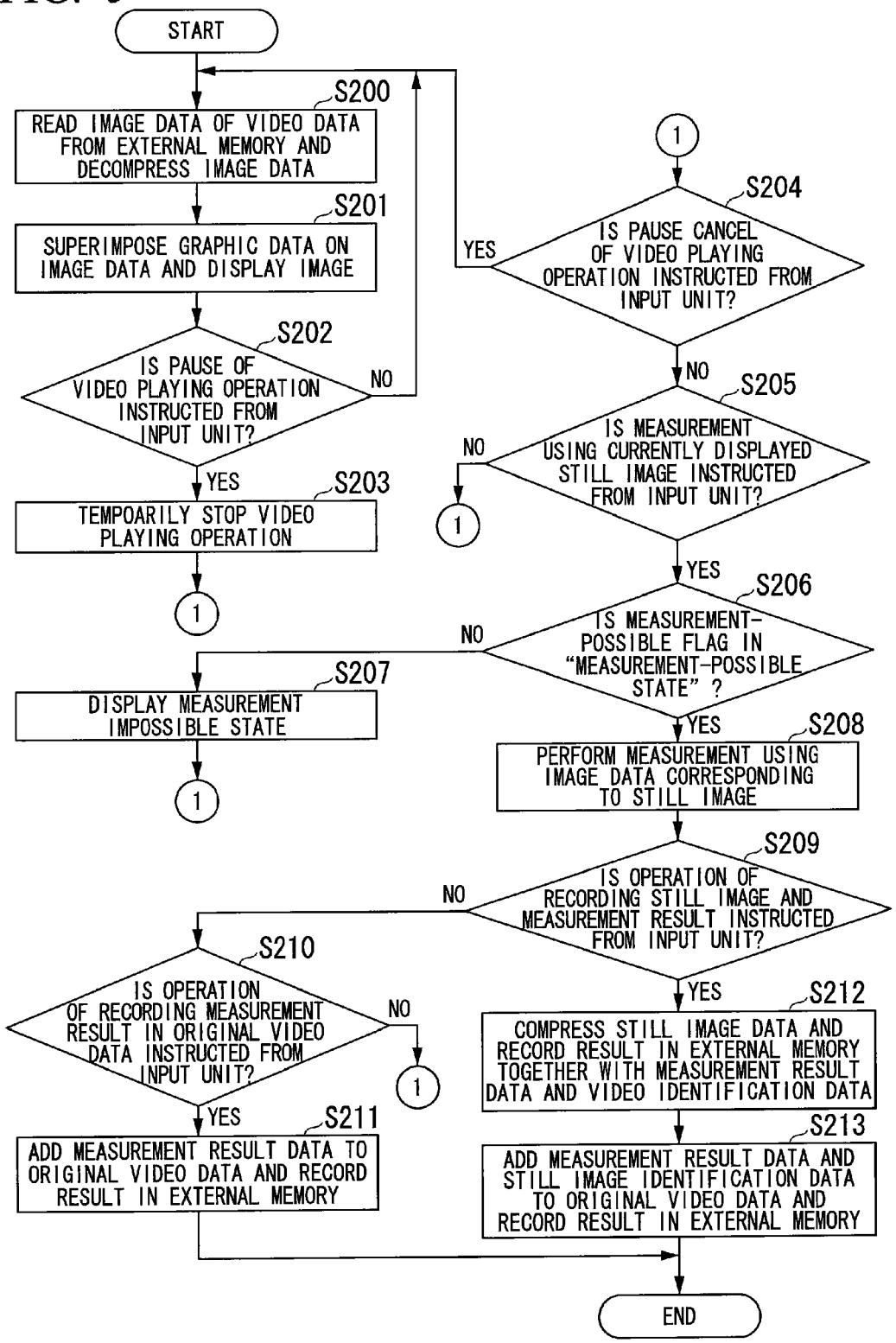
FIG. 5 is a flowchart showing a sequence of an operation (playing) of the endoscope apparatus according to the embodiment of the present invention.

FIG. 5 shows a sequence of an operation of playing the video data which has been recorded according to the sequence shown in FIG. 4. First, the CPU 103 reads from the external memory 30 the image data of one frame or field of the video data which has been recorded in the external memory 30, and decompresses the image data by using the codec unit 102 (Step S200).

Subsequently, the CPU 103 creates graphic data to be superimposed on the image data decompressed by the codec unit 102, and outputs the graphic data to the graphic superimposing unit 104. The graphic superimposing unit 104 creates a display signal by superimposing the graphic data created by the CPU 103 on the image data decompressed by the codec unit 102. The display unit 105 displays an image on the basis of the display signal (Step S201).

Figure 6:
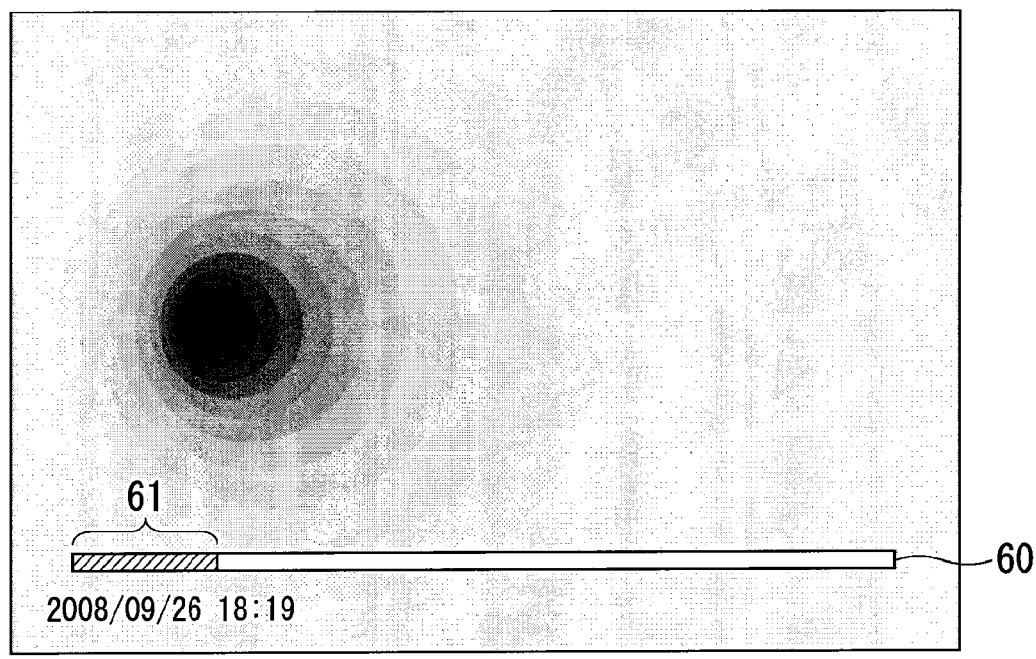
FIG. 6 is a reference diagram showing a displayed image when playing a video according to the embodiment of the present invention.

FIG. 6 shows an image displayed on the display unit 105 when playing the video. On the screen of the display unit 105, a play progress bar 60 is displayed together with information regarding a date, and the subject image. The play progress bar 60 shows a degree of video play progress. In the play progress bar 60, a hatched portion 61 shows the degree of progress. In order to display the play progress bar 60, the CPU 103 calculates a degree of progress on the basis of, for example, a time code given to the video data, and creates graphic data for displaying the play progress bar 60 based on the degree of progress.

After Step S201, the CPU 103 determines whether or not the pause of the video playing operation is instructed by the user, on the basis of the signal output from the input unit 107 (Step S202). In the case where the pause of the video playing operation is not instructed by the user, the process returns to Step S200. In the case where the pause of the video playing operation is instructed by the user, the CPU 103 temporarily stops the video playing operation (Step S203). At this time, an image based on the last played image data is displayed as a still image on the display unit 105.

Subsequently, the CPU 103 determines whether or not the pause cancel of the video playing operation is instructed by the user, on the basis of the signal output from the input unit 107 (Step S204). In the case where the pause cancel of the video playing operation is instructed by the user, the process returns to Step S200, and the video playing operation is resumed. In the case where the pause cancel of the video playing operation is not instructed by the user, the CPU 103 determines whether or not the measurement using the currently displayed still image is instructed by the user, on the basis of the signal output from the input unit 107 (Step S205).

In the case where the measurement using the currently displayed still image is not instructed by the user, the process returns to Step S204. In the case where the measurement using the currently displayed still image is instructed by the user, the CPU 103 determines whether or not the measurement-possible flag, which is added to the image data corresponding to the currently displayed still image, is in a "measurement-possible state" (Step S206).

In this embodiment, the measurement-possible flag is included in the control data. However, the control data may not include a measurement-possible flag and the measurement-possible state may be determined on the basis of the optical adapter type data or the like.

In the case where the measurement-possible flag is not in the "measurement-possible state", the CPU 103 creates graphic data showing that the measurement is impossible. As a result, the measurement-impossible state is displayed on the display unit 105 (Step S207). Subsequently, the process returns to Step S204.

In the case where the measurement-possible flag is in the "measurement-possible state", the CPU 103 performs measurement by using the last played image data, which corresponds to the displayed still image. At this time, the CPU 103 reads from the memory unit 106 the correction data corresponding to the optical adapter type data of the last played image data, corrects the image data on the basis of the correction data, and then performs the measurement (Step S208). The user is able to designate a measurement position on the still image by using the input unit 107. In addition, before measurement, image processes such as a noise reduction, an edge enhancement, and an interpolation may be performed on the image data.

Subsequently, the CPU 103 determines whether or not an operation of recording the still image data and the measurement result is instructed by the user, on the basis of the signal input from the input unit 107 (Step S209). In the case where the operation of recording the still image data and the measurement result is not instructed by the user, the CPU 103 determines whether or not the operation of recording the measurement result in the original video data is instructed by the user, on the basis of the signal input from the input unit 107 (Step S210).

In the case where the operation of recording the measurement result in the original video data is not instructed by the user, the process returns to Step S204. In addition, in the case where the operation of recording the measurement result in the original video data is instructed by the user, the CPU 103 adds to the original video data the measurement result data and measurement identification data (third identification information) for the identification of the frame or field used for measurement, and records the result in the external memory 30 (Step S211).

Meanwhile, in the case where the operation of recording the still image data and the measurement result is instructed by the user in Step S209, the CPU 103 compresses the still image data, which is image data of one frame or field of the video data, by using the codec unit 102, adds the measurement result data and video identification data (second identification information) to the compressed still image data, and then records the result in the external memory 30. The video identification data is used for the identification of the original video data corresponding to the still image data and the identification of the frame or field of the video data corresponding to the still image data, and is added to the header region 50 in FIG. 3 (Step S212).

Subsequently, the CPU 103 adds the measurement result data, the measurement identification data, and still image identification data (first identification information) to the original video data, and records the result in the external memory 30. The still image identification data is used for the identification of the still image data corresponding to the image data of the frame or field used for measurement. The still image identification data is added to the header portion 40 in FIG. 2 or to the various data of the unit data 42 (Step S213). Since the measurement result data is added to the still image data corresponding to the video data, the measurement result data may not be added to the video data.

By means of the video identification data and the still image identification data as described above, it is possible to correlate the still image data used for measurement with the original video data of the still image data. As described below, by using the video identification data and the still image identification data, it is possible to switch the current display of displaying the video to the display of the still image used for measurement. Alternatively, it is also possible to switch the current display of displaying the still image used for measurement to the display of the video.

Figure 7:
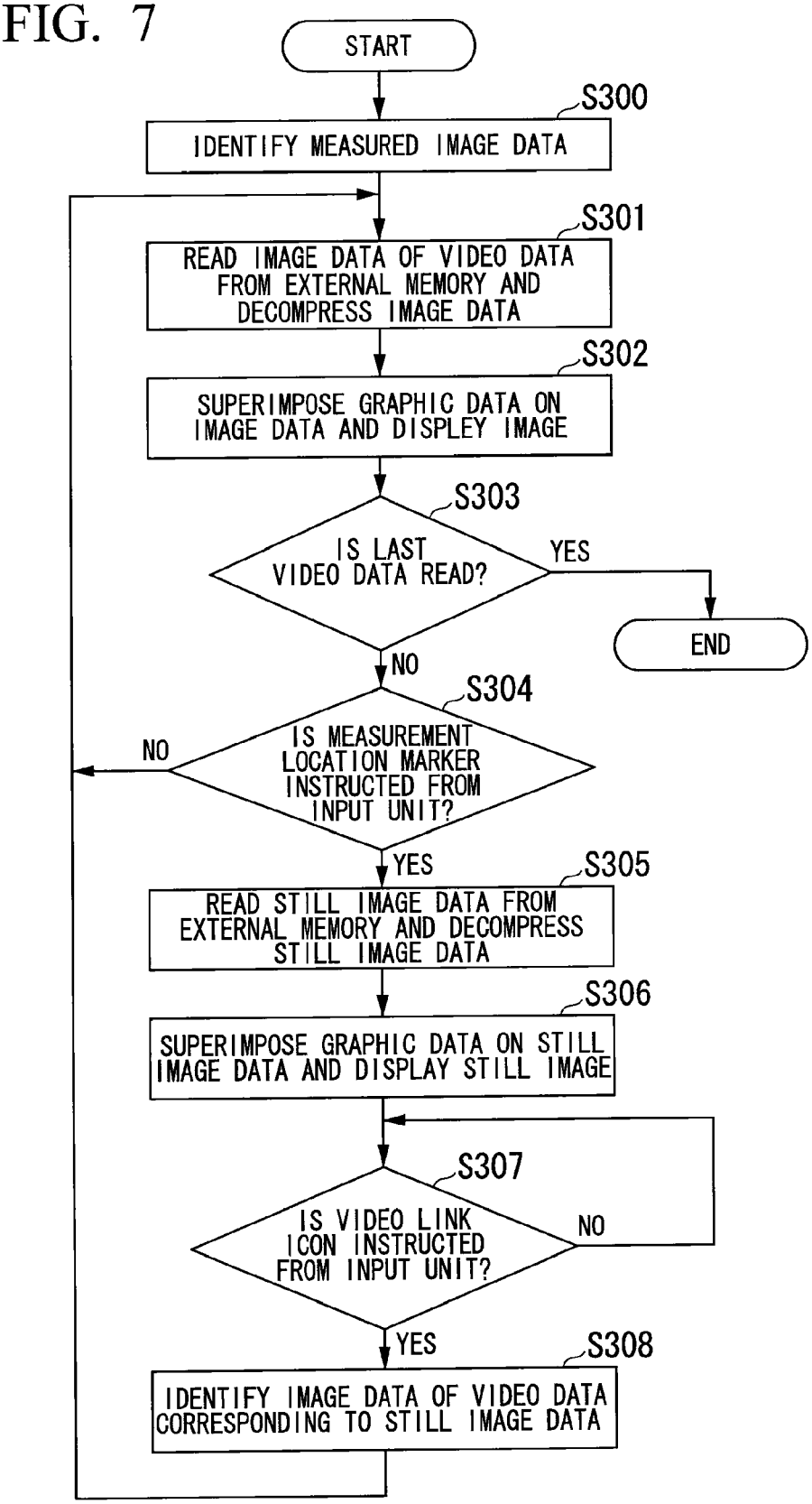
FIG. 7 is a flowchart showing a sequence of an operation (playing) of the endoscope apparatus according to the embodiment of the present invention.

FIG. 7 shows a sequence of an operation of playing the video data which is used for measurement and is recorded according to the sequence shown in FIG. 5. It is assumed that the video data to be played is already designated by the user. First, the CPU 103 reads from the external memory 30 the measurement identification data which is added to the video data, identifies the image data of the frame or field used for measurement on the basis of the measurement identification data, and then holds the information (Step S300).

Subsequently, the CPU 103 reads from the external memory 30 the image data of one frame or field of the video data recorded in the external memory 30, and decompresses the image data by using the codec unit 102 (Step S301).

Subsequently, the CPU 103 creates graphic data to be superimposed on the image data decompressed by the codec unit 102, and outputs the graphic data to the graphic superimposing unit 104. The graphic superimposing data 104 creates a display signal by superimposing the graphic data created by the CPU 103 on the image data decompressed by the codec unit 102. The display unit 105 displays an image based on the display signal (Step S302).

Figure 8:
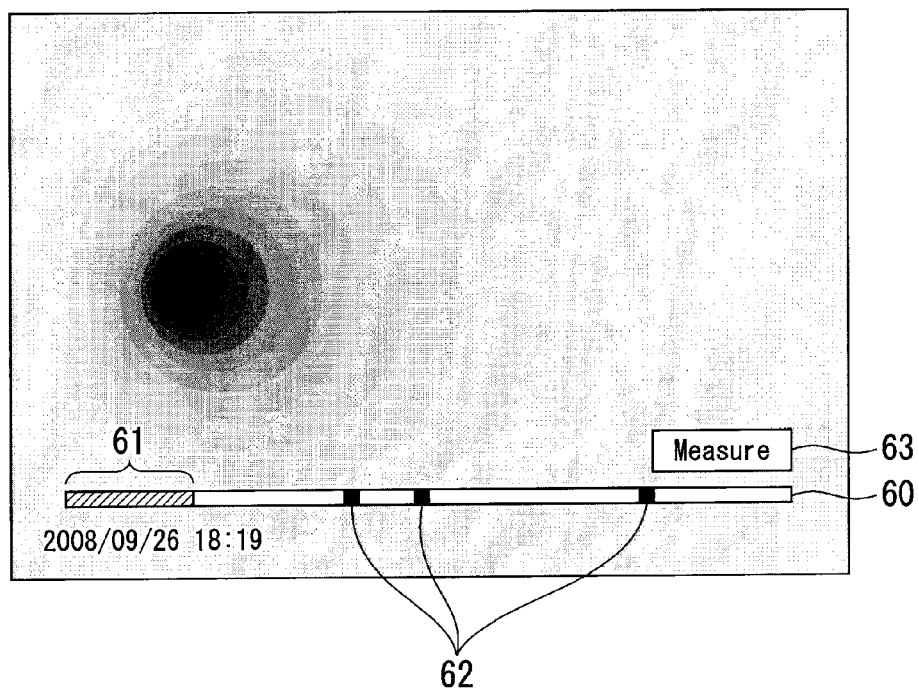
FIG. 8 is a reference diagram showing a displayed image when playing a video according to the embodiment of the present invention.

FIG. 8 shows an image displayed on the display unit 105 when playing the video. On the screen of the display unit 105, the play progress bar 60 is displayed together with the information regarding the date, and the subject image. In the play progress bar 60, the hatched portion 61 shows the degree of video play progress. A measurement location marker 62 for showing the temporal location of the frame or field used for measurement is displayed on the play progress bar 60. Further, a measurement icon 63 is displayed for showing show whether or not the measurement by using the image data of the displayed frame or field is possible.

In order to display the play progress bar 60, the CPU 103 calculates a degree of progress on the basis of, for example, a time code given to the video data. In addition, the CPU 103 identifies the location of the frame or field used for measurement on the basis of the information held in Step S300.

In addition, the CPU 103 determines whether or not the measurement is possible on the basis of the measurement-possible flag for the displayed frame or field. Then, the CPU 103 creates graphic data for displaying the play progress bar 60 and the measurement icon 63.

After Step S301, the CPU 103 determines whether or not the video data is read until the last frame or field (Step S303). In the case where the video data is read until the last frame or field, the video playing operation ends. In addition, in the case where the video data is not read until the last frame or field, the CPU 103 determines whether or not the measurement location marker is designated by the user, on the basis of the signal output from the input unit 107 (Step S304).

In the case where the measurement location marker is not designated by the user, the process returns to Step S301. In addition, in the case where the measurement location marker is designated by the user, the CPU 103 identifies the frame or field corresponding to the designated measurement location marker. Further, the CPU 103 identifies and reads from the external memory 30 the still image data corresponding to the frame or field by using the still image identification data, and decompresses the still image data by using the codec unit 102 (Step S305).

Subsequently, the CPU 103 creates graphic data to be superimposed on the still image data decompressed by the codec unit 102, and outputs the graphic data to the graphic superimposing unit 104. The graphic superimposing unit 104 creates a display signal by superimposing the graphic data created by the CPU 103 on the still image data decompressed by the codec unit 102. The display unit 105 displays a still image on the basis of the display signal (Step S306).

Figure 9:
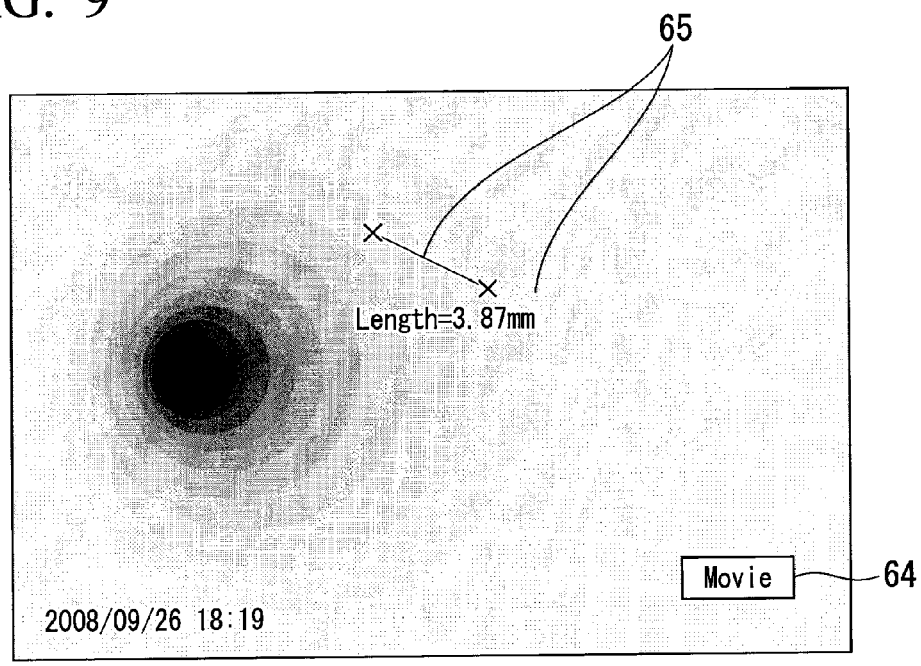
FIG. 9 is a reference diagram showing a displayed image when playing a still image according to the embodiment of the present invention.

FIG. 9 shows an image displayed on the display unit 105 when playing the still image. On the screen of the display unit 105, a measurement result 65 and a video link icon 64 are displayed together with the information regarding the date and the subject image. The video link icon 64 is an icon for allowing the user to instruct the play of the video data corresponding to the still image data. In order to display the image shown in FIG. 9, the CPU 103 creates graphic data for displaying the measurement result 65 and the video link icon 64.

After Step S306, the CPU 103 determines whether or not the video link icon is designated by the user, on the basis of the signal output from the input unit 107 (Step S307). In the case where the video link icon is not designated by the user, the process returns to Step S307. In the case where the video link icon is designated by the user, the CPU 103 identifies the video data corresponding to the still image data, and identifies the image data of the frame or field of the video data corresponding to the still image data, by using the video identification data added to the still image data (Step S308). Subsequently, the process returns to Step S301, and the video data is played again from the frame or field identified in Step S308.

In the operation shown in FIG. 7, in the case where the video data is played until the frame or field corresponding to the measurement location marker, the video playing operation may stop. Alternatively, in the same case, the video playing operation may be temporarily stopped, and the video playing operation may be continued after a predetermined elapsed time. Alternatively, only the image data of the frame or field corresponding to the measurement location marker may be played as a slideshow. At this time, the measurement result may be displayed, or an icon for showing the measurement result may be displayed.

In the case where the measurement location marker is designated in Step S304, the image data of the frame or field corresponding to the measurement location marker among the image data constituting the video data is played, and a still image based on the image data may be displayed. At this time, the measurement result may be displayed, or an icon for showing the measurement result may be displayed.

Further, the still image may first be displayed by playing the still image data the still image data, and in the case where the video playing operation is instructed by the user, the video may be displayed by playing the video data identified by the video identification data from the frame or field identified by the video identification data.

As described above, according to this embodiment, it is possible to read the video data recorded in the external memory 30, and to perform the measurement on the basis of the image data of the arbitrary frame or field of the video data. For this reason, even when a user misses the optimal measurement timing, it is possible to reattempt the measurement at the optimal timing, and to perform the measurement by selecting the image data suitable for measurement. Accordingly, it is possible to improve convenience of the measurement.

In addition, since the measurement-possible state is determined on the basis of the measurement-possible flag or the like included in the control data, it is possible to prevent a degradation of the measurement accuracy due to, for example, measurement using image data which is not suitable for measurement. In addition, since the measurement is performed after correcting the image data by using the correction data corresponding to the type of optical adapter 20 which is shown by the optical adapter type data included in the control data, it is possible to prevent a degradation of the measurement precision.

Further, since the measurement result is added to the image data used for measurement at the time of playing the video, and the result is recorded as the still image data in the external memory 30, it is possible to review later the measurement result and the subject state at the time of measurement by using the still image data.

Furthermore, since the still image data used for measurement is correlated with the original video data of the still image data, it is possible to more improve convenience of the measurement. In this embodiment, as shown in FIG. 7, it is possible to switch the current display of displaying the video to the display of the still image used for measurement, and to switch the current display of displaying the still image used for measurement to the display of the video. Accordingly, it is possible for the user to easily check the measurement result in accordance with the purpose.

Moreover, as shown in FIG. 8, since the measurement location marker showing the temporal location of the frame or field used for measurement is displayed when playing the video, it is possible for the user to easily recognize the measurement timing.

While preferred embodiments of the present invention have been described and illustrated above, it should be understood that these are exemplary of the present invention and are not to be considered as limiting. Additions, omissions, substitutions, and other modifications can be made without departing from the spirit or scope of the present invention. Accordingly, the present invention is not to be considered as being limited by the foregoing description, and is only limited by the scope of the appended claims.

What is claimed is:

1. An endoscope apparatus comprising:
an imaging unit which continuously captures a subject image formed by an optical system to create a video signal of a site of observation;
a creating unit which creates a measurement-possible flag indicating whether or not measurement is possible for every frame of image data of the video signal, the measurement-possible flag being created based on information on a state of the endoscope apparatus including all of: (i) a type of the optical system, (ii) whether or not an image process which influences measurement accuracy is being performed, and (iii) a format of the image data;
a recording unit which records video data and control data on a recording medium, wherein the video data comprises the frames of image data, and wherein the control data includes the measurement-possible flag for each of the frames of image data and is used to control a measurement operation;
a reading unit which reads the video data and the control data from the recording medium; and
a measuring unit which determines whether or not the measurement operation is possible based on the measurement-possible flag included in the control data read by the reading unit, and when it is determined that the measurement operation is possible, performs the measurement operation based on the image data of the video data read by the reading unit, wherein the measurement operation is a three-dimensional measurement operation.

2. The endoscope apparatus according to claim 1, wherein the control data includes optical system type data indicating the type of the optical system.

3. The endoscope apparatus according to claim 1, wherein the recording unit adds a measurement result to the image data on which the measuring unit performs the measurement operation, and records the measurement result as still image data on the recording medium.

4. The endoscope apparatus according to claim 3, wherein the recording unit adds first identification information, which is used to identify the still image data corresponding to the image data on which the measuring unit performs the measurement operation, to the video data read by the reading unit, and records the result on the recording medium.

5. The endoscope apparatus according to claim 4, wherein when the image data measured by the measuring unit is designated in a state in which the reading unit reads, from the recording medium, the control data and the video data containing the first identification information added thereto, the reading unit reads from the recording medium the still image data corresponding to the designated image data based on the first identification information.

6. The endoscope apparatus according to claim 3, wherein the recording unit adds second identification information, which is used to identify image data in the video data corresponding to the still image data, to the still image data, and records a result of the addition on the recording medium.

7. The endoscope apparatus according to claim 6, wherein when the video data is designated in a state in which the reading unit reads the still image data from the recording medium, the reading unit begins reading the video data from the image data corresponding to the still image data based on the second identification information.

8. The endoscope apparatus according to claim 3, wherein the recording unit adds third identification information, which is used to identify image data on which the measuring unit performs the measurement operation, to the video data read by the reading unit, and records a result of the addition on the recording medium.

9. The endoscope apparatus according to claim 8, further comprising:
    a display signal creating unit which creates a display signal for displaying a video based on the video data read by the reading unit;
    wherein the reading unit reads the control data and the video data having the third identification information added thereto, and the display signal creating unit creates the display signal for displaying the video and a temporal location of the image data identified by the third identification information.

10. A method of controlling an endoscope apparatus including a processor to perform functions comprising:
    continuously capturing a subject image formed by an optical system to create a video signal of a site of observation;
    creating a measurement-possible flag indicating whether or not measurement is possible for every frame of image data of the video signal, the measurement-possible flag being created based on information on a state of the endoscope apparatus including all of: (i) a type of the optical system, (ii) whether or not an image process which influences measurement accuracy is being performed, and (iii) a format of the image data;
    recording video data and control data on a recording medium, wherein the video data comprises the frames of image data, and wherein the control data includes the measurement-possible flag for each of the frames of image data and is used to control a measurement operation;
    reading the video data and the control data from the recording medium; and
    determining whether or not the measurement operation is possible based on the measurement-possible flag included in the control data read from the recording medium, and when it is determined that the measurement operation is possible, performing the measurement operation based on the image data of the video data read from the recording medium, wherein the measurement operation is a three-dimensional measurement operation.

11. The endoscope apparatus according to claim 2, wherein the measuring unit corrects the image data based on correction data corresponding to the type of the optical system indicated by the optical system type data, and performs the measurement operation based on the corrected image data.

12. The endoscope apparatus according to claim 1, wherein the recording unit records, on the recording medium, data including a header region including the control data and a data region including the frames of image data of the video data.

13. The endoscope apparatus according to claim 1, wherein the recording unit records, on the recording medium, a plurality of unit data each including one of the frames of image data of the video data and the control data corresponding to the image data.

* * * * *